United States Patent
Varkuti et al.

(10) Patent No.: US 10,463,320 B2
(45) Date of Patent: *Nov. 5, 2019

(54) METHOD FOR OPTIMISING THE POSITION OF A PATIENT'S BODY PART RELATIVE TO AN IMAGING DEVICE

(71) Applicant: Brainlab AG, Munich (DE)

(72) Inventors: Bálint Varkuti, Munich (DE); Harald Braun, Munich (DE)

(73) Assignee: Brainlab AG, Munich (DE)

( * ) Notice: Subject to any disclaimer, the term of this patent is extended or adjusted under 35 U.S.C. 154(b) by 203 days.

This patent is subject to a terminal disclaimer.

(21) Appl. No.: 15/537,573

(22) PCT Filed: Dec. 18, 2015

(86) PCT No.: PCT/EP2015/080555
§ 371 (c)(1),
(2) Date: Jun. 19, 2017

(87) PCT Pub. No.: WO2016/097323
PCT Pub. Date: Jun. 23, 2016

(65) Prior Publication Data
US 2018/0263577 A1    Sep. 20, 2018

(30) Foreign Application Priority Data

Dec. 19, 2014   (WO) .................. PCT/EP2014/078733

(51) Int. Cl.
*A61B 6/00* (2006.01)
*A61B 6/04* (2006.01)
(Continued)

(52) U.S. Cl.
CPC ............ *A61B 6/0492* (2013.01); *A61B 6/032* (2013.01); *A61B 6/0421* (2013.01); *A61B 6/12* (2013.01);
(Continued)

(58) Field of Classification Search
CPC ......... A61B 90/11; A61B 90/14; A61B 6/032; A61B 6/0421; A61B 6/12; A61B 6/501;
(Continued)

(56) References Cited

U.S. PATENT DOCUMENTS 7,677,802 B2   3/2010   Haras
7,925,328 B2   4/2011   Urquhart et al.
(Continued)

FOREIGN PATENT DOCUMENTS

DE   10 2007 052 65 A1   5/2008
EP       2159725 A1      3/2010
(Continued)

OTHER PUBLICATIONS

EPO, International Search Report and Written Opinion for corresponding PCT/EP2015/080555, dated Apr. 24, 2016, pp. 1-9.
(Continued)

*Primary Examiner* — Kiho Kim
(74) *Attorney, Agent, or Firm* — Tucker Ellis LLP

(57) ABSTRACT

The present invention relates to positioning a patient's body part including a target relative to an imaging device that generates a radiation beam directed towards the target. Geometry data is received that describes the geometry of at least one structure located in the field of view of the imaging device. Tracking date is received that describes the spatial location and/or orientation of the at least one structure within the field of view of the imaging device. Position data is determined that incorporates the geometry date and the tracking data. The position data describes whether the location and/or orientation of the at least one structure with respect to an image trajectory is desirable. Repositioning data is determined that describes a desired location and/or orientation of the at least one structure with respect to the
(Continued)

Figure 1:
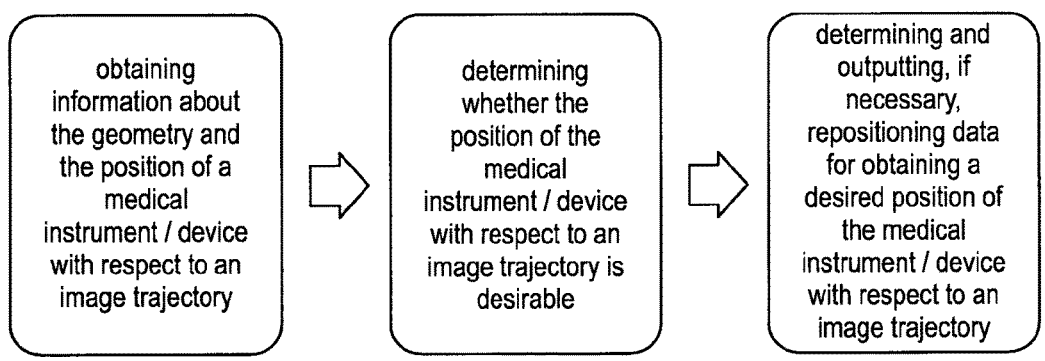

obtaining information about the geometry and the position of a medical instrument / device with respect to an image trajectory  determining whether the position of the medical instrument / device with respect to an image trajectory is desirable  determining and outputting, if necessary, repositioning data for obtaining a desired position of the medical instrument / device with respect to an image trajectory image trajectory. The repositioning data is output to allow repositioning of the at least one structure.

15 Claims, 1 Drawing Sheet

(51) Int. Cl.

| | |
|---|---|
| G16H 40/63 | (2018.01) |
| A61N 5/10 | (2006.01) |
| A61B 6/03 | (2006.01) |
| A61B 6/12 | (2006.01) |
| A61B 90/11 | (2016.01) |
| A61B 90/14 | (2016.01) |
| A61B 10/02 | (2006.01) |
| G06F 19/00 | (2018.01) |

(52) U.S. Cl.
CPC .......... *A61B 6/501* (2013.01); *A61B 6/5258* (2013.01); *A61B 6/547* (2013.01); *A61B 10/02* (2013.01); *A61B 90/11* (2016.02); *A61B 90/14* (2016.02); *A61N 5/1049* (2013.01); *G06F 19/00* (2013.01); *G06F 19/321* (2013.01); *G16H 40/63* (2018.01); *A61N 2005/1051* (2013.01); *A61N 2005/1097* (2013.01); *G06F 19/3481* (2013.01)

(58) Field of Classification Search
CPC ....... A61B 6/5258; A61B 6/547; A61B 10/02; A61N 5/1049; A61N 2005/1051; A61N 2005/1097; G16H 40/63; G06F 19/00; G06F 19/321; G06F 19/3481
See application file for complete search history.

(56) References Cited

U.S. PATENT DOCUMENTS

| | | | | |
|---|---|---|---|---|
| 8,971,490 | B2* | 3/2015 | Maurer, Jr. | A61B 6/12 |
| | | | | 378/65 |
| 9,433,387 | B2* | 9/2016 | Ahn | A61B 6/04 |
| 9,721,379 | B2* | 8/2017 | Zino | A61B 6/12 |
| 2005/0182316 | A1* | 8/2005 | Burdette | A61B 8/0833 |
| | | | | 600/424 |
| 2013/0345543 | A1* | 12/2013 | Steibel, Jr. | A61B 6/467 |
| | | | | 600/407 |
| 2014/0046212 | A1* | 2/2014 | Deutschmann | A61B 6/03 |
| | | | | 600/567 |
| 2015/0038765 | A1* | 2/2015 | Vilsmeier | G06T 7/246 |
| | | | | 600/1 |
| 2017/0340297 | A1* | 11/2017 | Varkuti | A61N 5/1049 |
| 2018/0047183 | A1* | 2/2018 | Berlinger | G06T 7/74 |

FOREIGN PATENT DOCUMENTS

| | | |
|---|---|---|
| EP | 2740405 A1 | 11/2014 |
| WO | 99278839 A2 | 6/1999 |
| WO | 2006017838 A2 | 2/2006 |
| WO | 2016096038 A1 | 6/2016 |

OTHER PUBLICATIONS

Wang, "Novel Techniques for Integrating Video Augmented X-ray Imaging into Orthopedic and Trauma Surgery", Chair for Computer Aided Medical Procedures & Augmented Reality, Dissertation, Mar. 20, 2012, Technische Universität Müchen,Germany, p. 1-170.

* cited by examiner

METHOD FOR OPTIMISING THE POSITION OF A PATIENT'S BODY PART RELATIVE TO AN IMAGING DEVICE

RELATED APPLICATION DATA

This application is a national phase application of International Application No. PCT/EP2015/080555, filed Dec. 18, 2015 and published in the English language. International Application No. PCT/EP2015/080555 is a divisional of International Application No. PCT/EP2014/078733, filed Dec. 19, 2014.

The present invention relates to a data processing method, performed by a computer, for positioning a patient's body part including a target to be depicted by means of an imaging device relative to an imaging device, particularly an irradiation source of a radiation imaging device, that generates a radiation beam directed towards the target, and to a corresponding computer program and system. The method according to the present invention may also optimise positioning of a patient's body and/or parts of a medical installation relative to an imaging device, particularly irradiation source.

For medical procedures such as navigated surgery it is important to know the exact spatial position, i. e. the spatial location and/or the spatial orientation of medical instruments or devices within the patient's body. Surgical instruments are known, which are to be introduced along a predetermined trajectory. For those instruments guides are provided so as to ensure that the instruments are advanced along the desired trajectory. As some instruments cannot be tracked directly by means of a medical tracking system, imaging procedures may be help in verifying the correct placement of such instruments or devices within the patient's body.

The present invention provides a method that helps in verifying the correct placement of medical instruments or devices by utilizing 2D-images such as ultrasound images or x-ray-images. Those images cannot be taken from an arbitrary direction without the risk of obscuring important features of the instrument or device which indicate the spatial location and/or orientation of the instrument or device. Therefore, the features of each instrument or device define certain directions in which an image is preferably taken so as to obtain the information needed. It is therefore desirable to place the image device in a desired location and/or orientation with respect to the instrument or device at its place of destination in a target area to be depicted.

The method, the program and the system are defined by the appended independent claims 1, 14 and 15. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

A first embodiment of the inventive method comprises the steps of:
    receiving, at the processor, geometry data describing the geometry of at least one structure located in the field of view of the imaging device;
    receiving, at the processor, tracking data describing the spatial location and/or orientation of the at least one structure within the field of view of the imaging device;
    determining, with the processor, position data incorporating the geometry data and the tracking data, describing whether the location and/or orientation of the at least one structure with respect to an image trajectory, particularly a radiation beam trajectory through the target is desirable;
    determining, with the processor, repositioning data describing a desired location and/or orientation of the at least one structure with respect to the image trajectory, particularly the radiation beam trajectory through the target;
    outputting, from the processor, the repositioning data allowing for repositioning of the at least one structure.

In other words, the inventive method considers detailed knowledge of the spatial relationship between a target to be depicted, an imaging device and at least one structure which should be placed adjacent to the target in a desired location and/or orientation. Therefore, the invention considers the geometry/shape of objects and structures which lie within the field of view of the imaging device.

This additional knowledge can then be used to calculate an optimised position of the objects/structures within the field of view of the imaging device so as to verify a correct placement of a medical instrument or device.

For example, the imaging device may be a x-ray-imaging device that may move, relative to a patient lying on a support structure such as a table, wherein the patient or at least a patient's body part can be immobilised relative to the support structure. For example, the patient's head can be fixed relative to the table via a headring. In case of the stereotactic surgery, the patient's head may further be provided with an articulated support structure such as a stereotactic arc which supports a biopsy needle. Since all of those structures may contain material that interferes with a radiation beam, it is desirable to move any object which may unintentionally interfere with the radiation beam away from the radiation beam trajectory. Additionally or alternatively, it can be desirable to avoid sensitive anatomical structures (such as the patient's eyes) to be hit by the radiation beam during image acquisition. With the position and the geometry of the objects/structures during image acquisition known, an optimal position of the patient and/or a medical installation during image acquisition can be calculated and the patient and/or the medical installation may be optimally positioned or re-positioned before an image acquisition procedure is started. The repositioning data may indicate that the current position is already sufficient to avoid corrupted images or radiation damage. It may however also indicate that the current position must be altered, so that the patient and/or critical structures will have to be repositioned.

According to another embodiment of the present invention, the spatial position of at least one critical structure is obtained:
    via a marker device attached to said structure, which is detectable by a medical tracking system; and/or
    via a position transmission device transmitting the spatial position of said structure to a medical navigation system; and/or
    from at least one registered cross-sectional-image showing the structure; and/or
    from an anatomical atlas indicating the spatial position of the anatomical structure relative to the patient's body part.

For example, any structure which may interfere with the radiation beam, thereby causing corrupted images, may be provided with a marker device, so that the spatial position of said structure relative to the imaging device and the target can be calculated. Additionally or alternatively, any structure may be provided with a device, for example an actuator used to move a medical structure, that determines the structure's spatial position and transmits this data to a medical navigation system.

It is however also conceivable that, at least initially, the spatial position of any structure is obtained from a cross-sectional-image such as a CT-image or a MR-image, which may be registered to the coordinate system of the imaging device. For determining the spatial position of sensitive anatomical structures, it is also conceivable to take this data from an anatomical atlas registered with the patient or the patient's body part.

Moreover, the geometry of at least one critical structure may be obtained:
  from a database; and/or
  from at least one registered cross-sectional-image showing the structure
  from an anatomical atlas indicating the geometry of the anatomical structure relative to the patient's body part.

For example, the geometry of any medical instrument or device may be stored in a database, for example a database of the navigation system. However, the geometry of any medical device or any anatomical structure may be taken from a cross-sectional image such as a CT-image or a MR-image which may be registered to the coordinate system of the imaging device. For anatomical structures, it is again conceivable that the geometry of the anatomical structure is obtained from an anatomical atlas which may also indicate the spatial position of the anatomical structure. It is also possible to provide data, for example from an anatomical atlas, that indicates absorption and/or reflection properties of anatomical structures. The patient may then be positioned to avoid the beam to pass strongly reflecting or absorbing tissue.

The position of the target region of interest may be determined
  automatically or manually from at least one registered cross-sectional-image showing the target;
  anatomically or manually from at least one registered 2D transmission image; and/or
  manually by the use of a tracked pointer instrument.

For example, the target position as well as the target size and/or geometry may be taken from at least one CT-image and/or MR-image, wherein contrast enhanced CT-imaging may be performed in order to highlight critical structures which are to avoid by the radiation beam. A tracked pointer instrument could be utilised to mark an area of interest, i.e. the target to be irradiated.

With the position and geometry of critical structures as well as at least the position of the target of interest known with respect to the imaging device, it is possible to calculate whether a critical structure lies within the radiation beam trajectory when the target is irradiated. It is therefore also possible to determine whether or not it is necessary to re-position either the patient relative to the imaging device (or the imaging device relative to the patient), or additionally or alternatively, to alter the relative position of a critical structure relative to the target of interest, so as to possibly obtain a position for which no critical structure lies within the beam trajectory when the target is irradiated. It is also conceivable to move critical structures as far as possible away from the beam trajectory, so as to minimise possible interference with the beam and resulting artefacts.

For example, the patient may be positioned or repositioned together with the patient table, an immobilising headring and/or a stereotactic arc relative to the imaging device. This may comprise any rotational and/or translational movement of the patient. Additionally or alternatively, the imaging device, for example the x-ray-device may be positioned or repositioned relative to the patient. Additionally or alternatively, it may be sufficient to position or reposition one or more critical structures such as a headring or a stereotactical arc relative to the patient so that the irradiation beam does not hit those critical structures when the target is irradiated. Again, positioning or repositioning may comprise any rotational and/or translational movement.

It will become clear that the inventive method may be used to automatically position or reposition the patient or critical structures relative to the imaging device. To do so, actuators may move the patient and/or critical structures based on data that is output and that describes an optimal position of the patient and/or critical structures relative to the imaging device. In the alternative however, it is also conceivable that instructions based on data describing an optimal position is output to a practitioner, for example via a user interface, who may then manually position the patient and/or critical structures. It is to be noted that the inventive method may be performed to initially obtain an optimised position before an image scan is performed, as well as it may be also used to reposition the patient and/or structures for a subsequent image acquisition procedure.

The data obtained may be also used to reduce the radiation intensity of the radiation beam for an anatomical structure having a high sensitivity to radiation damage and lying within the radiation beam trajectory. For example, the radiation intensity may be reduced for areas lying outside the target region, and which contain sensitive structures. By doing so, the target region is irradiated in the intended manner, but without applying excessive radiation to surrounding anatomical structures.

According to the present invention, the orientation of any medical instrument, for example a biopsy device may be considered for repositioning the patient and/or critical medical structures.

For example, it is desirable that a biopsy needle inserted into a patient's brain is oriented as far as possible perpendicular to the viewing direction of the imaging device. By doing so, intra-operative imaging used to verify a correct placement of the biopsy needle is improved.

A further aspect of the present invention refers to a program which, when running on a computer, causes the computer to perform the method steps of any method described herein and/or a program storage medium on which the program is stored, for example in a non-transitory form.

A further aspect of the present invention relates to a system for positioning a target of a patient's body part relative to an irradiation source of a radiation imaging device, generating a radiation beam directed towards the target, comprising a computer on which a program as described above is stored and/or run.

The present invention may be applied to any 2D imaging method or device, in particular an x-ray imaging procedure or device.

Terminology of the present disclosure is described in the following, and the following description also forms part of the present disclosure.

The method in accordance with the invention is for example a data processing method. The data processing method is preferably performed using technical means, for example a computer. The data processing method is preferably constituted to be executed by or on a computer and for example is executed by or on the computer. For example, all the steps or merely some of the steps (i.e. less than the total number of steps) of the method in accordance with the invention can be executed by a computer. The computer for example comprises a processor and a memory in order to process the data, for example electronically and/or optically. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data"/"receiving data" for example encompasses (within the framework of a data processing method) the scenario in which the data are determined by the data processing method or program. Determining data for example encompasses measuring physical quantities and transforming the measured values into data, for example digital data, and/or computing the data by means of a computer and for example within the framework of the method in accordance with the invention. The meaning of "acquiring data"/"receiving data" also for example encompasses the scenario in which the data are received or retrieved by the data processing method, processor or program, for example from another program, a previous method step or a data storage medium, for example for further processing by the data processing method, processor or program. The expression "acquiring data"/"receiving data" can therefore also for example mean waiting to receive data and/or receiving the data. The received data can for example be inputted via an interface. The expression "acquiring data"/"receiving data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The method in accordance with the invention is preferably at least partly executed by a computer, i.e. all the steps or merely some of the steps (i.e. less than the total number of steps) of the method in accordance with the invention can be executed by a computer.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising:

the computer of the preceding claim, for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

The present invention is also directed to a navigation system for computer-assisted surgery. This navigation system preferably comprises the aforementioned computer for processing the data provided in accordance with the data processing method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder facing the marker and assists in placing the marker device on the marker holder in a force fit and/or positive fit.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

In the following, the invention is described with reference to the enclosed figures which represent preferred embodiments of the invention. The scope of the invention is not however limited to the specific features disclosed in the figures, which show:

FIG. 1 shows a specific embodiment of the inventive method.

FIG. 1 shows the basic steps of the inventive method which can be performed during intra-operative image acquisition, as well.

At first, a patient is placed on a patient table and the patient's head is immobilized relative to the table for performing a medical procedure so as to place a DBS-stimulation-device having a directional electrode. For such an oriented device it is relevant to plan not only the trajectory along which the lead is entered into its final end-position within a target region, but it is also important to know the orientation of the directional electrode since it influences the efficiency of the stimulation. If the electrode points in a wrong direction, the target cannot be optimally stimulated. In case of a biopsy needle being placed within a patient, a small tumour of about 1 cm$^3$ volume could be missed by a needle orifice pointing away from the tumour.

An "optimal" depiction of the DBS-stimulation lead depends on the direction in which the specific feature (electrode or needle orifice) is oriented. For example, a one-dimensional shape-alteration of an elongated instrument can be best seen in an image which has been taken in a direction that is perpendicular to the direction of the shape-alteration.

A pre-operative treatment plan contains a three-dimensional model of the stimulation lead, so it is known in which directions the electrodes have to be oriented.

If it is known what type of imaging device will be used during surgery, for example an x-ray-device that can only make sagittal images of the brain, it can be determined whether the feature of interest, i.e. the at least one directional electrode will be sufficiently depicted in order to verify its desired orientation.

Now the location and/or orientation of all structures can be optimised to have an optimal imaging set up later during surgery. In case the orientation of the imaging device is invariant, all other artificial and/or anatomical structures can be moved into place so that an optimal image can be made from the DBS-stimulation lead.

Alternatively, for an invariant position of the patient, the planed trajectory of the instrument or device can be altered and optimised to obtain an optimal image for this specific OR, with this specific x-ray-imaging device and with this specific stereotactic arc.

Further, it is possible to decide whether to make an image of the whole DBS-stimulation lead or whether to make an image of the electrode only, in case the extension of the electrode along the lead trajectory is known. It is also possible to provide a separate directionality marker the direction of which can be identified on the two-dimensional image, and which therefore indicates the direction of the medical instrument or device.

The invention claimed is:

1. A method for positioning a patient's body part including a target relative to an imaging device that generates a radiation beam directed towards the target, the method being implemented by a processor of a computer and comprising the following steps:
    receiving, at the processor, geometry data describing a geometry of at least one structure located in a field of view of the imaging device;
    receiving, at the processor, tracking data describing a spatial location or orientation of the at least one structure within the field of view of the imaging device;
    determining, with the processor, position data incorporating the geometry data and the tracking data and describing whether the location or orientation of the at least one structure with respect to an image trajectory is desirable;
    determining, with the processor, repositioning data describing a desired location or orientation of the at least one structure with respect to the image trajectory; and
    outputting, from the processor, the repositioning data allowing for repositioning of the at least one structure.

2. The method according to claim 1, wherein the at least one structure is a medical device or instrument, which is introduced into the patient's body part.

3. The method according to claim 2, wherein the medical device or instrument comprises at least one portion defining at least one preferred direction for a 2D-image which, when made of the medical device or instrument in said preferred direction, provides information about a spatial location and/or orientation of said at least one portion, and wherein the desired location or orientation of the at least one structure corresponds to the at least one preferred direction.

4. The method according to claim 3, wherein recognisable properties of the medical device or instrument within said portion differ from recognisable properties of the medical device or instrument outside said portion in said 2D-image made in said at least one preferred direction.

5. The method according to claim 3, wherein the 2D-image provides biunique information about a location or orientation of said at least one portion with respect to an overall location or orientation of the medical device or instrument.

6. The method according to claim 2, wherein said medical device or instrument is selected from the group consisting of:
    a biopsy needle having at least one orifice for obtaining a cell-sample;
    a medical marker having a shape indicative of at least one spatial position and/or orientation; and
    a stimulation lead having at least one directional electrode.

7. The method according to claim 3, wherein determining the position data or the repositioning data involves identifying a spatial location or orientation of other structures which inhibit an ability of said 2D-image to provide information about the spatial location or orientation of said at least one portion of said medical device or instrument.

8. The method according to claim 1,
wherein information about the spatial location or orientation of the at least one structure is obtained:
via a marker device attached to said at least one structure, which is detectable by a medical tracking system; or
via a position transmission device transmitting the spatial position of said at least one structure to a medical navigation system; and
wherein the geometry of at least one structure is obtained from a database.

9. The method according to claim 1, wherein the patient's body part is immobilized via an immobilization structure relative to a support structure.

10. The method according to claim 1, wherein said repositioning data output is used to automatically reposition the patient's body part or the at least one structure relative to said imaging device, or to output instructions to manually reposition the patient's body part or the at least one structure relative to said imaging device.

11. The method according to claim 1, wherein a position of the patient's body part together with the at least one structure positionally fixed to the patient's body part is altered relative to the imaging device so as to obtain a desired position of the at least one structure with respect to a radiation beam trajectory through the target.

12. The method according to claim 1, wherein a position of the at least one structure is altered relative to the patient's body part so as to obtain a desired position of the at least one structure with respect to a radiation beam trajectory through the target.

13. The method according to claim 1, wherein a position of the target is determined:
automatically or manually from at least one registered cross-sectional image showing the target;
automatically or manually from at least one registered 2D transmission image; or
manually by use of a tracked pointer instrument.

14. A non-transitory, computer-readable storage medium having stored thereon computer-executable instructions for a program which, when executed by a computer, causes the computer to:

receive geometry data describing a geometry of at least one structure located in a field of a view of an imaging device that generates a radiation beam directed towards a target;
receive tracking data describing a spatial location or orientation of the at least one structure within the field of view of the imaging device;
determine position data incorporating the geometry data and the tracking data, the position data describing whether the spatial location or orientation of the at least one structure with respect to an image trajectory is desirable;
determine repositioning data describing a desired location or orientation of the at least one structure with respect to the image trajectory; and
output the repositioning data to enable repositioning of the at least one structure.

15. A system for positioning a target of a patient's body part relative to an imaging device that generates a radiation beam directed towards the target, the system comprising:
a processor; and
a memory storing computer-executable instructions for a program that, when executed by the processor, configure the processor to:
receive geometry data describing a geometry of at least one structure located in a field of a view of the imaging device;
receive tracking data describing a spatial location or orientation of the at least one structure within the field of view of the imaging device;
determine position data incorporating the geometry data and the tracking data, the position data describing whether the spatial location or orientation of the at least one structure with respect to an image trajectory of the imaging device is desirable;
determine repositioning data describing a desired location or orientation of the at least one structure with respect to the image trajectory of the imaging device; and
output the repositioning data to enable repositioning of the at least one structure with relative to the imaging device.

* * * * *